United States Patent [19]

Umezawa et al.

[11] Patent Number: 4,719,231

[45] Date of Patent: Jan. 12, 1988

[54] 3-[N-(MERCAPTOACYL)]AMINO-4-ARYL-BUTANOIC ACID DERIVATIVES AND AN ANALGESIC AGENT COMPRISING THE SAME

[75] Inventors: Hamao Umezawa; Tomio Takeuchi, both of Tokyo; Takaaki Aoyagi, Fujisawa; Mitsugu Hachisu, Yokohama; Masao Hirayama, Yokosuka; Shinjiro Murata, Yokohama; Shunzo Fukatsu, Tokyo, all of Japan

[73] Assignee: Zaidan Hojin Biseibutsu Kagaku Kenkyu Kai, Tokyo, Japan

[21] Appl. No.: 735,643

[22] Filed: May 20, 1985

[30] Foreign Application Priority Data

May 25, 1984 [JP] Japan ................. 59-104669

[51] Int. Cl.$^4$ ............... C07C 153/017; C07C 153/023; C07C 149/41; C07C 149/43

[52] U.S. Cl. .................. 514/513; 558/254; 564/162; 560/16; 562/426; 514/562; 514/540; 514/538

[58] Field of Search ............ 558/254; 564/162; 560/16; 562/426; 514/562, 513, 540, 538

[56] References Cited

U.S. PATENT DOCUMENTS 3,897,480  7/1975  Mita et al. ..................... 558/254

Primary Examiner—Henry R. Jiles
Assistant Examiner—Robert C. Whittenbaugh
Attorney, Agent, or Firm—Larson and Taylor

[57] ABSTRACT

New 3-[N-(mercaptoacyl)]amino-4-arylbutanoic acid derivatives are now provided, which exhibit analgesic activity and are effective to enhance the analgesia induced by a known analgesic compound, ]D-ala$^2$,met$^5$]-enkephalin (DAME).

6 Claims, No Drawings

3-[N-(MERCAPTOACYL)]AMINO-4-ARYL-BUTANOIC ACID DERIVATIVES AND AN ANALGESIC AGENT COMPRISING THE SAME

SUMMARY OF THE INVENTION

This invention relates to new compounds having an analgesic activity, and more particularly to 3-[N-(mercaptoacyl)]amino-4-arylbutanoic acid derivatives and pharmaceutically acceptable salts thereof. This invention also relates to a new analgesic agent comprising said new compounds as the active ingredient.

BACKGROUND OF THE INVENTION

It is known that enkephalin or endorphin as the analgesic peptide exists in the brain of mammalian animals, and particularly enkephalin is existing at a high level in the vesicles of the nervous cells at the nerve terminal in the brain, and also that enkephalinase is co-existing in the same areas as those where enkephalin is found. Besides, the possibility that enkephalin functions as neurotransmitters in the central nervous system of mammalian animals is suggested in the "Nature" Vol. 276, pages 523 to 526 (1980).

Furthermore, it has been revealed that acupuncture analgesia is mediated through release of the analgesic peptides such as enkephalins and endorphins in the brain (see: "Acta Physiologica Scandinavia" Vol. 100, 382~384 (1977). It is also reported that possibility that the analgesic activity of morphine is relying on that morphine plays a role to cause enkephalin to be released in the nervous system and be bound to opiate receptors (see: the "Life Science" No. 25, pages 53 to 60 (1979)).

We have taken the above facts into consideration and take it that an inhibitor against enkephalinase will show an analgesic activity as it is administered alone, and it is expected that the inhibitor against enkephalinase will be highly effective for eliminating or minimizing the pain of such patients who feel chronic pain owing to a low level of enkephalins or high activity of enkephalinase in the brain. It is also expected that an enkephalinase-inhibitor will be useful as an aid for enhancing the acupuncture analgesia and morphine analgesia (see: the "Showa Igakukai Zasshi" Vol. 39, No. 5, pages 543 to 550 (1979)).

In an attempt to provide a new analgesic compound, therefore, we have extensively researched on the inhibitory activity of various known and new compounds against enkephalinase. As a result, we have previously found that some of bestatin-related compounds and some derivatives of 3-amino-2-hydroxy-4-phenyl-butanoic acid show an analgesic activity as examined in animals. Based on these findings, we proposed an analgesic agent comprising these above compounds as the active ingredient [see: Japanese Patent Application First Publication (KOKAI) No. 67516/1982 and No. 65260/1983; as well as U.S. Pat. Nos. 4,395,402 and 4,474,764.].

In a further development of our research, we have examined, for the same screening purpose, new compounds, 3-[N-(mercaptoacyl)]amino-4-arylbutanoic acid and its various derivatives as newly synthesized by us, for their inhibitory activity against enkephalinase. As a result, now, we have found that a class of the new derivatives examined exhibit an useful analgesic activity, and we have reached this invention.

DETAILED DESCRIPTION OF THE INVENTION

According to the first aspect of this invention, therefore, there is provided as the new compound a 3-[N-(mercaptoacyl)]amino-4-arylbutanoic acid derivative of the formula (1):

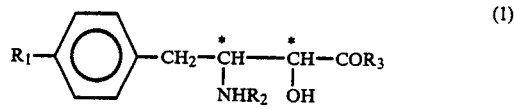

wherein $R_1$ is a hydrogen atom or a hydroxyl group; $R_2$ is an S-substituted or unsubstituted mercaptoacyl group of the formula:

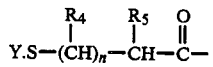

where Y is a hydrogen atom, a lower ($C_2$-$C_5$)alkanoyl group or a benzoyl group; n is a whole number of zero or 1; $R_4$ is a hydrogen atom, a lower ($C_1$-$C_4$)alkyl group or a phenyl group; $R_5$ is a hydrogen atom, a lower ($C_1$-$C_4$)alkyl group, a phenyl group, a hydroxyl group or an amino group; and $R_3$ is a hydroxyl group, a lower ($C_1$-$C_4$)alkoxygroup or an α-amino acid residue bonded by the peptide linkage; and the asterisk (*) denotes the R-configuration or the S-configuration or a combination thereof, and a pharmaceutically acceptable salt of said 3-[N-(mercaptoacyl)]amino-4-arylbutanoic acid derivative.

In the definition of said alkyl group, alkoxyl group and alkanoyl group in this specification, by the term "lower" is meant that the alkyl moiety in these groups contains 1 to 4 carbon atoms.

The compounds of the general formula (1) above may be deemed as a derivative of 3-amino-2-hydroxy-4-phenylbutanoic acid (abbreviated as AHPA). When the group $R_2$ connected to 3-amino group in the general formula (1) is such one as represented by the formula:

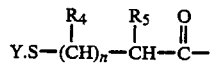

wherein Y is a hydrogen atom, said group $R_2$ may be termed as a 2-mercaptoacyl group or a 3-mercaptoacyl group. Similarly, when Y is a lower alkanoyl group or a benzoyl group in the formula just above, said group $R_2$ may be termed as a 2-(acylthio)acyl group or 3-(acylthio)acyl group.

When the new compound of the general formula (1) is such one of the formula (1) where the group $R_3$ denotes a hydroxyl group, the whole compound of the formula (1) is in the form of a free carboxylic acid. When the new compound of the general formula (1) is such one of the formula (1) where the group $R_3$ is a lower alkoxyl group, the whole compound of the formula (1) is in the form of a carboxylic acid alkyl ester. When the new compound of the general formula (1) is such one of the formula (1) where the group $R_3$ is an α-amino acid residue bonded by the peptide linkage (—CO—NH—), the group $R_3$ may be an α-amino acid residue such as the residue of glycine, alanine, phenylalanine, leucine, isoleucine or arginine or the like. These α-amino acid residue may be either in the D-form or in the L-form. Particular examples of said α-amino acid residue as the group $R_3$ are as follows:

| | |
|---|---|
| Glycine residue | —NH—CH$_2$—COOH |
| Alanine residue | —NH—CH(CH$_3$)—COOH |
| Phenylalanine residue | —NH—CH—COOH<br>　　　　　｜<br>　　　　　CH$_2$<br>　　　　　｜<br>　　　　　C$_6$H$_5$ |
| Leucine residue | —NH—CH—COOH<br>　　　　　｜<br>　　　　　CH$_2$CH(CH$_3$)$_2$ |
| Isoleucine residue | —NH—CH—COOH<br>　　　　　｜<br>　　　　　CH—CH$_3$<br>　　　　　｜<br>　　　　　C$_2$H$_5$ |
| Arginine residue | —NH—CH—COOH<br>　　　　　｜<br>　　　　　(CH$_2$)$_3$—NH—C—NH$_2$<br>　　　　　　　　　　　‖<br>　　　　　　　　　　　NH |

According to a particular embodiment of the first aspect of this invention, there is provided as the new compound a 3-[N-(mercaptoalkanoyl)]amino-4-phenylbutanoic acid of the formula (1a)

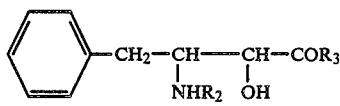
　　　　　　　　　　　　　　　　　　　(1a)

wherein $R_2$ is mercaptoacetyl group, acetylthioacetyl group, benzoylthioacetyl group, mercaptopropionyl group, acetylthiopropionyl group, benzoylthiopropionyl group, or 2-amino-3-mercaptopropionyl group (i.e., cysteinyl group —CO—CH(NH$_2$)—CH$_2$—SH), and $R_3$ is a hydroxyl group, a (C$_1$-C$_4$)alkoxy group, a glycine residue of the formula —NH—CH$_2$—COOH or a leucine residue of the formula

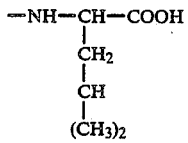

and a pharmaceutically acceptable salt of said 3-[N-(mercaptoalkanoyl)]amino-4-phenylbutanoic acid.

The method for the production of the new compound of the general formula (1) are now described. Generally, the compound of the formula (1) according to this invention may be produced by (a) reacting the 3-amino group of 3-amino-2-hydroxy-4-phenylbutanoic acid (abbreviated as AHPA) or 3-amino-2-hydroxy-4-p-hydroxyphenyl-butanoic acid (abbreviated as p-hydroxy-AHPA) (including various steric isomers of these acids), or a lower alkyl ester of these acids (AHPA, p-hydroxy-AHPA) or such dipeptide as obtained by condensation of an α-amino acid with AHPA or p-hydroxy-AHPA, represented by the general formula (2):

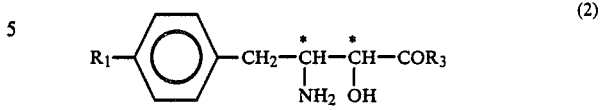
　　　　　　　　　　　　　　　　　　　(2)

wherein $R_1$ is a hydrogen atom or a hydroxyl group; $R_3$ is a hydroxyl group, a lower alkoxyl group or an α-amino acid residue attached by the peptide linkage (—CO—NH—), and the asterisk (*) denotes that the carbon atoms to which the asterisk (*) is attaching may take the R-configuration or the S-configuration or a combination thereof, with a 2- or 3-haloalkanoyl halide represented by the general formula (3):

$$X_1-(CH)_n-\overset{R_5'}{\underset{|}{CH}}-COX_2 \qquad (3)$$
$$\overset{|}{R_4}$$

wherein $R_4$ and n are defined as above; $R_5'$ is a hydrogen atom, a lower alkyl group, a phenyl group or a hydroxyl group or a protected amino group; $X_1$ and $X_2$ may be the same or different and are each a halogen atom, (b) reacting the resulting condensation product compound of the formula

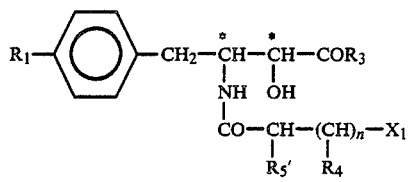

wherein $R_1$, $R_3$, $R_4$, $R_5'$, $X_1$, n and the asterisk are as defined above, with a mercaptane compound of the general formula (4)

Y'SH　　　　　　　　　　　　　　　　(4)

wherein Y' is a lower alkanoyl group such as acetyl, or a benzoyl group, and then, if necessary, (c) removing from the resulting reaction product compound of the formula

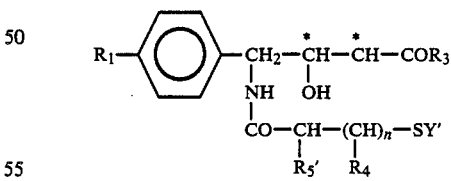

wherein $R_1$, $R_3$, $R_4$, $R_5'$, Y', n and the asterisk are as defined above, the S-acyl group (Y') and any protecting group (where exist) in a known manner.

The compounds of the general formula (1) according to this invention may preferably be prepared by the method as described below:

The 3-amino group of the starting compound of the formula (2) in the form of the carboxylic acid or the ester thereof, or the dipeptide, is firstly acylated by reacting with the haloalkanoyl halide of the general formula (3). This acylation reaction may be performed in an aqueous medium of alkaline nature, such as a diluted aqueous solution of an alkali metal hydroxide e.g. sodium hydroxide, an aqueous solution of an alkali metal hydrogen carbonate and an aqueous solution of an alkali metal carbonate, at a relatively low temperature, for example, of 0° C. to 30° C. The resulting acylation product is then subjected to a substitution reaction with the anion of the thioacid or thiol compound of the general formula (4) to give the desired product of this invention. This substitution reaction may be carried out in an alkaline aqueous medium, preferably in an aqueous solution of an alkali metal carbonate in a known manner. And, if required, the substitution reaction product so obtained as above may be subsequently subjected to hydrolysis under alkaline conditions (for example, using an aqueous solution of an alkali metal hydroxide), in order to remove the protective S-acyl group (Y') and any protective group (where exists) and thereby to give the new compound of this invention according to the general formula (1) where Y is the hydrogen atom.

The compound of the general formula (1) where $R_5$ (in the group $R_2$) is an amino group may also be produced by condensing the 3-amino group of the compound of the general formula (2').

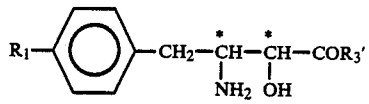

(2')

wherein $R_1$ and the asterisk * are as defined above; $R_3'$ is a lower alkoxyl group or an α-amino acid alkyl ester residue bonded by the peptide linkage, with the compound of the general formula (5):

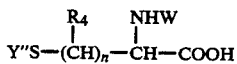

(5)

wherein $R_4$ and n are as defined above; Y" is a mercapto-protecting group such as a lower alkanoyl group, a benzoyl group, an acetoaminomethyl group or another similar mercapto-protecting group; and W is an amino-protecting group such as a benzyloxycarbonyl group, a t-butyloxycarbonyl group or another similar amino-protective group, in a manner known per se in the conventional synthesis of peptides, and then, if required, removing from the resulting condensation product compound the residual protecting groups (Y", W) in a known manner. This condensation reaction may be performed according to a known carbodiimide method using dicyclohexyl-carbodiimide (DCC) as the dehydration agent, or according to a known active ester method using N-hydroxysuccinimide ester.

The resulting reaction mixture containing the desired condensation product may be treated by conventional procedures for isolation and purification to give the desired product compound in a purified form. The compound of the general formula (1) may easily be converted, in a conventional manner, into the form of an intermolecular salt, free carboxylic acid, free base, a metal salt (carboxylate) such as sodium salt, an acid-addition salt with an inorganic acid such as hydrochloride, or a salt with amine such as dicyclohexylamine, or an alkyl ester such as ethyl ester.

The starting compounds of the general formula (2) and of the general formula (2') are all known ones. The preparation of (2S,3R)-AHPA is described in Japanese patent application First Publication "Kokai" No. 1361189/1977, and the preparation of p-hydroxy AHPA is described in Japanese patent application First Publication "Kokai" No. 79248/1979 (see U.S. Pat. No. 4,189,604). The stereo isomeres of these compounds may be synthesized by the method of Kato et al (see: "J. Chem. Soc." Perkin 1, (1980), page 1618). The starting compounds of the general formula (2) and (2') wherein $R_3$ or $R_3'$ is a lower alkoxyl group or an α-amino acid residue bonded by the peptide linkage, may also be prepared from (2S,3R)-AHPA and p-hydroxy-AHPA as the initial material.

According to a second aspect of this invention, there is provided a pharmaceutical composition, useful as analgesic agent, which comprises as the active ingredient, a compound of the formula (1) or the formula (1a) as defined hereinbefore or a pharmaceutically acceptable salt thereof.

According to a third aspect of this invention, there is provided a method of therapeutically treating an animal feeling pain, including humans feeling pain, which comprises administering to the animal, a compound of the formula (1) or a compound of the formula (1a) or a pharmaceutically acceptable salt thereof, in a non-toxic and effective amount sufficient to reduce or eliminate the pain.

According to a fourth aspect of this invention, there is provided a method of enhancing the analgesic activity of a known analgesic compound, [D-ala$^2$,met$^5$]enkehalin (DAME) when administered to an animal feeling pain, including humans feeling pain, which comprises administering an effective and non-toxic amount of a compound of the formula (1) or a compound of the formula (1a) or a pharmaceutically acceptable salt thereof to the animal, just before or at the same time as when DAME is given to the animal for the analgesic purpose.

The pharmaceutical composition of this invention, owing to its analgesic activity, may be utilized for the analgesic or antinociceptive treatment of pain in animals, including men. The composition of this invention may be given orally, parenterally or intrarectally or even intramedullarily or intraspinally e.g. by intralumbar puncture and may be formulated into a suitable form for the route of administration employed. Composition in the form of injectable solution may contain 0.1% to 10.0% by weight of the compound of the formula (1) or (1a) as active ingredient, and also one or more of a pH-adjuster, buffer, stabilizer, local anesthetics and an additive for rendering the solution isotonic. The injectable solution may be prepared to be adapted for subcutaneous, intramuscular or intravenous injection by any conventional pharmaceutical technique. Solid composition for oral administration which may be in the form of tablets, coated tablets, granules, powder and capsules, may contain excipients for the active ingredient, and if required, other additives, including disintegrators, lubricants, colorants, flavors and the like. The proportion of the active compound to the carrier may be at a ratio of 1:1 to 1:100 by weight and may usually be chosen appropriately depending on the form of the orally administrable formulation prepared. The optimal dosage of the compound of the formula (1) or (1a) administered will, of course, depend on the mode of administration, sex, body weight, age, disease conditions of the patients and the treatment aimed. By way of guideline, for men, the unit dosage generally contains from 20 mg to 2 g of the compound of the formula (1) or (1a) which may be given to an adult person one or more times per day.

The high analgesic activity of the compounds of the general formula (1) or (1A) according to this invention is now described with reference to the following experiments.

Particular examples of the compounds according to this invention as tested in the following experiments are as follows. After the compound name is shown the abbreviation of the compound in each parenthesis.

(1) (2S,3R)-3-[N-(acetylthioacetyl)]amino-2-hydroxy-4-phenylbutanoic acid [abbreviated as (2S,3R)-N-(AcSCH$_2$CO)AHPA]

(2) (2S,3R)-3-[N-(mercaptoacetyl)]amino-2-hydroxy-4-phenylbutanoic acid [abbreviated as (2S,3R)-N-(HSCH$_2$CO)AHPA]

(3) (2S,3S)-3-[N-(acetylthioacetyl)]amino-2-hydroxy-4-phenylbutanoic acid [abbreviated as (2S,3S)-N-(AcSCH$_2$CO)AHPA]

(4) (2S,3S)-3-[N-(mercaptoacetyl)]amino-2-hydroxy-4-phenylbutanoic acid [abbreviated as (2S,3S)-N-(HSCH$_2$CO)AHPA]

(5) (2S,3R)-3-(N-L-Cysteinyl)amino-2-hydroxy-4-phenylbutanoic acid [abbreviated as (2S,3R)-N-(L-Cys)-AHPA]

(6) N-{(2S,3R)-3-[N-(acetylthioacetyl)]amino-2-hydroxy-4-phenylbutanoyl}glycine [abbreviated as (2S,3R)-N-(AcSCH$_2$CO)-AHPA-Gly]

(7) N-{(2S,3R)-3-[N-(acetylthioacetyl)]amino-2-hydroxy-4-phenylbutanoyl}-L-leucine [abbreviated as (2S,3R)-N-(AcSCH$_2$CO)-AHPA-L-Leu]

(8) (2S,3R)-3-[N-(2-benzoylthiopropionyl)]amino-2-hydroxy-4-phenylbutanoic acid [abbreviated as (2S,3R)-N-(BzSCH(Me)CO)-AHPA]

(9) (2S,3R)-3-[N-(3-benzoylthiopropionyl)]amino-2-hydroxy-4-phenylbutanoic acid [abbreviated as (2S,3R)-N-(BzSCH$_2$CH$_2$CO)-AHPA]

EXPERIMENT 1

Inhibitory activity against enkephalinase

Testing method

A preparation of enkephalinase was made by homogenizing corpus striatum of rat brain and by partial purification of the brain homogenate according to the method of Gorenstein et al (see: the "Life Science" vol. 25, 2065~2070 (1979)).

A test compound as identified in Table 1 below was dissolved in a mixture of Tris-hydrochloride buffered solution (pH 7.7) and an aqueous 1% Triton×100 (an active surfactant) to such a concentration that the added quantity of the test compound amounted to one-tenth of the volume of said mixture. To the solution of the test compound so prepared was added the enkephalinase, followed by incubation for 5 minutes at ambient temperature and the resulting mixture was admixed with methionine-enkephaline as the substrate. The reaction mixture so prepared was incubated for 1 hour at 37° C. and then subjected to a high-performance liquid chromatography in such a manner that the Tyr-Gly-Gly (a fragment of the methionine-enkephaline) formed by the enzymatic degradation of the methionine-enkephaline was isolated and the quantity of Tyr-Gly-Gly was determined by an electro-chemical detector. In this way, IC$_{50}$ value of the test compound, namely, the dose of the test compound required for 50% inhibition of the enkephalinase was measured.

The test results are shown in the Table 1.

TABLE 1

| Test compound | Inhibitory activity against enkephalinase, IC$_{50}$ (mM) |
| --- | --- |
| (2S,3R)-N-(AcSCH$_2$CO)-AHPA | 0.05 |
| (2S,3R)-N-(HSCH$_2$CO)-AHPA | 0.003 |
| (2S,3S)-N-(AcSCH$_2$CO)-AHPA | 0.3 |
| (2S,3S)-N-(HSCH$_2$CO)-AHPA | 0.02 |
| (2S,3R)-N-(L-Cys)-AHPA | 0.04 |
| (2S,3R)-N-(AcSCH$_2$CO)-AHPA-Gly | >0.3 |
| (2S,3R)-N-(AcSCH2CO)-AHPA-L-Leu | >0.3 |
| (2S,3R)-N-(BzSCH(Me)CO)-AHPA | >0.3 |
| (2S,3R)-N-(BzSCH$_2$CH$_2$CO)-AHPA | >0.3 |
| (2S,3R)-AHPA (comparative) | 14.0 |
| (2S,3R)-AHPA-L-Leu (comparative) | 0.59 |

EXPERIMENT 2

Effect of enhancing the analgesia by [D-ala$^2$,met$^5$]enkephaline (abbreviated as DAME)

Testing method

A known analgesic compound, DAME and the particular compound under test of this invention were administered into the brain of the test rats by puncture of cerebroventride.

Thus, the test compound was administered into the brain of the rats using a metal cannula of 400 μm in external diameter which had been inserted into the ventriculus lateralis cerebri in a brain region of 3.2 mm anterior from the bregma, 0 mm from the central line and 0.7 mm in depth, of the brain. [see "L. J. Pellegrino and A. J. Cushman; A Stereotaxic Atras of the Rat Brain. Appleton-Century-Crofts, Division of Meredith Publishing Co., New York, (1967)"]. The test for the estimation was commenced at such a time after 48 hours or more later than the end of the surgical operation when the test rats were deemed as having recovered from the damages induced by the surgical operation. Analgesia tests were conducted using the rats having been closely restrained in a wire mesh cage, according to the tail-flick latency method (see: Hachisu et al., Life Sciences, 30, 1739–1746 (1982)). Analgesic activity was evaluated in term of the value of percentage of increase in the tail-flick latency time of the test rats receiving the test compound, as compared with the control rats receiving no test compound. The power of the radiant heat source was adjusted to give a tail-flick latency value (as the control value) of about 2 seconds for the rats before the administration of the test compound.

The cut-off of 7 seconds was used in order to prevent the tail tissues from being damaged by the heat. The maximal percent effect (M.P.E) of the tail-flick latency test was calculated according to the following equation:

$$M.P.E. = \frac{(\text{The tail-flick latency(sec.) of the test rats receiving test compound}) - (\text{The tail-flick latency(sec.) of the control rats})}{7.0 - (\text{The tail-flick latency(sec.) of the control rats})} \times 100$$

The test results obtained are shown in the Table 2 below.

TABLE 2

| Test compound | M.P.E. | | | Enhancement in the analgesia by DAME |
|---|---|---|---|---|
| | DAME 10 μg | Test compound 30 μg | DAME 10 μg + Test Compound 30 μg | |
| (2S,3R)-N—(L-Cys)—AHPA | 14.4 ± 4.2%* | 10.0 ± 5.2% | 87.0 ± 13.0%** | 604.2 |
| (2S,3R)-N—(AcSCH₂CO)AHPA | 16.2 ± 3.9%* | 13.1 ± 6.0% | 100 ± 0%** | 617.2 |

*P < 0.05,
**P < 0.01 (n = 3 − 4)

EXPERIMENT 3

Analgesic activity of test compound as estimated according to the acetic acid-writhing method Testing procedure Mice of ddy-strain (body weight 20 to 25 grams) were employed as the test animal. A suspension of the compound under test was subcutaneously injected in such a manner that said suspension as injected into each mouse provides the dosage of 30 mg/kg or 300 mg/kg of the test compound. 30 Minutes after the administration, an aqueous solution of 0.6% of acetic acid was injected intraperitoneally into the mice at a volume of 0.1 ml per 10 g of the body weight. 5 Minutes after the injection of the aqueous acetic acid, the estimation was commenced to count the number of the writhing reaction of the treated mice (the motions such as abdominal constrictions and extensions of the treated mice as induced by the injection of acetic acid) which took place for the subsequent 15 minutes.

The rate (%) of suppression of the writhing reaction by the test compound was evaluated according to the following equation:

The rate (%) of suppression =

$$\frac{\text{(Writhing number of the control mice receiving merely the solvent containing no test compound)} - \text{(Writhing number of the test mice receiving test compound)}}{\text{(Writhing number of the control mice receiving the solvent containing no test compound)}} \times 100$$

The test results are shown in Table 3.

TABLE 3

| Test compound | Dosage of test compound (mg/kg) | Rate of suppression (%) (average value ± S.E.) | The number of test animal |
|---|---|---|---|
| (2S,3R)-N—(L-Cys)—AHPA | 30 | 56.5 ± 9.9** | 11 |
| | 300 | 47.9 ± 11.9** | 12 |
| (2S,3R)-N—(AcSCH₂CO)—AHPA | 30 | 33.7 ± 13.5* | 11 |
| | 300 | 33.3 ± 13.4* | 11 |
| (2S,3R)-N—(HSCH₂CO)—AHPA | 30 | 12.5 ± 14.7 | 12 |
| | 300 | 36.5 ± 10.5* | 10 |

*P < 0.05,
**P < 0.01

From the foregoing data, it is clear that the new compounds of this invention exhibit the effect of inhibiting enkephalinase and also the effect of enhancing the analgesia by DAME. In the analgesic test according to the acetic acid writhing method, it was also observed that the new compounds of this invention alone show the analgesic activity.

From the foregoing, it is clear that the new compounds of this invention are useful as an analgesic or antinociceptive agent of new type when used alone or as an analgesic-acid which is useful to enhance the analgesic activity of DAME when it is administered in association with DAME.

This invention is now described with reference to the following Examples in which the preparation of the particular compounds according to this invention are illustrated.

EXAMPLE 1

Synthesis of (2S,3R)-3-[N-(acetylthioacetyl)]amino-2-hydroxy-4-phenylbutanoic acid (2S,3R)-AHPA(585 mg) was dissolved in 1N aqueous sodium hydroxide (3 ml) under ice-cooling. The solution obtained was admixed with 2N aqueous sodium hydroxide (1.5 ml), and then with chloroacety chloride (339 mg), followed by stirring for 10 minutes under ice-cooling and for 2 hours at ambient temperature. To the resulting reaction solution was added a mixture of thiolacetic acid (250 mg), potassium carbonate (288 mg) and water (3 ml), followed by stirring at ambient temperature overnight. The reaction mixture was adjusted to pH 1.5 with 1N HCl and was saturated with sodium chloride and extracted with ethyl acetate. The extract in ethyl acetate was dried over anhydrous sodium sulfate (Na₂SO₄), and distilled to remove the solvent therefrom, leaving a viscous residue. This residue was purified by chromatography on a column of silica gel as eluted with a mixture of chloroform-acetic acid (7:3), and a colorless powder of the titled compound (594 mg) was obtained. This product showed a value of 312 (M+1) in FD mass spectrometry.

PMR (in CDCl₃): 2.34 (s, 3H,

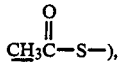

2.78 and 3.05 (ABq, 2H, —CH₂Ph), 3.50 (s, 2H, —SCH₂CO—), 4.10 (d, 1H, —CH(OH)CO—), 4.64 (q, 1H,

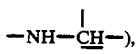

6.76 (d, 1H, —NH—) and 7.25 (s, 5H, aromatic protons) ppm.

EXAMPLE 2

Synthesis of (2S,3R)-3-[N-(mercaptoacetyl)]amino-2-hydroxy-4-phenylbutanoic acid (2S,3R)-3-[N-(acetylthioacetyl)]amino-2-hydroxy-4-phenylbutanoic acid (311 mg) obtained in Example 1 was added to degassed methanol (6 ml) under stream of nitrogen, and the mixture obtained was then mixed with 1N aqueous sodium hydroxide (2 ml), followed by stirring for one hour under ice-cooling. The reaction mixture as formed was distilled under reduced pressure to remove the methanol therefrom, and the residue obtained was taken into water (4 ml). The resulting aqueous solution was washed once with chloroform, and the aqueous phase was then adjusted to pH 1 with 1N HCl, followed by extraction with chloroform. The extract in chloroform was dried over anhydrous sodium sulfate (Na2SO4) and concentrated to give 230 mg of the titled compound as a colorless powder. This product gave a value of 270 (M+1) in FD mass spectrometry.

PMP (in CDCl3): 1.81 (t, 1H, HS—), 2.96 (d, 2H, —CH2Ph), 3.21 (t, 2H, —S—CH2—CO—), 4.13 (d, 1H, —CH(OH)CO—), 4.69 (q, 1H,

6.63 (br. s, —NH—) and 7.25 (s, 5H, aromatic protons) ppm.

EXAMPLE 3

Synthesis of (2S,3S)-3-[N-acetylthioacetyl)]amino-2-hydroxy-4-phenylbutanoic acid (2S,3S)-AHPA (58.5 mg) was dissolved in 1N aqueous sodium hydroxide (0.6 ml) under ice-cooling. To the solution was added chloroacetyl chloride (33.9 mg), followed by stirring for 10 minutes under ice-cooling and then for 2 hours at ambient temperature. To the reaction solution was further added a mixture of thiolacetic acid (CH3COSH) (25 mg), potassium carbonate (29 mg) and water (0.3 ml), and the resulting admixture was processed in the same manner as in Example 1 above, whereby 43.2 mg of the titled compound as a colorless powder was obtained. This product gave a value of 312 (M+1) in FD mass spectrometry.

PMR (in CDCl3): 2.25 (s, 3H,

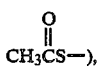

2.92 (d, 2H, —CH2Ph), 3.43 (s, 2H, —SCH2CO—), 4.38 (d, 1H, —CH(OH)CO—), 4.50 (br. s, 1H,

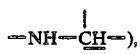

6.70 (br.s, 1H, —NH—), and 7.15 (s, 5H, aromatic protons) ppm.

EXAMPLE 4

Synthesis of (2S,3S)-3-[N-(mercaptoacetyl)]amino-2-hydroxy-4-phenylbutanoic acid (2S-3S)-3-[N-(acetylthioacetyl)]-amino-2-hydroxy-4-phenylbutanoic acid (31.1 mg) obtained in Example 3 was added to degassed methanol (1 ml) under stream of nitrogen, and the resultant mixture was admixed with 1N aqueous sodium hydroxide (0.2 ml), followed by stirring for one hour under ice-cooling. The reaction solution was distilled under reduced pressure to remove the methanol. The residue obtained was taken into water (1 ml). The aqueous mixture obtained was treated in the same manner as in Example 2, and 17 mg of the titled compound as a colorless powder was obtained. This product gave a value pf 270 (M+1) in FD mass spectrometry.

EXAMPLE 5

Synthesis of (2S,3R)-[N-L-cisteinyl]amino-2-hydroxy-4-phenylbutanoic acid (A) A mixture of (2S,3R)-3-amino-2-hydroxy-4-phenylbutanoic acid methylester hydrochloride (122 mg), N-methylmorpholine (0.055 ml), 1-hydroxybenzotriazole (67.3 mg) and tetrahydrofuran (1 ml) was admixed with N-t-butoxycarbonyl-S-acetoamidomethyl-L-cystein (146 mg) and water. The resulting mixture was mixed with dicyclohexylcarbodiimide (113 mg), followed by stirring for 4 hours under ice-cooling. To the reaction solutions was then added acetic acid (0.3 ml), followed by stirring further for 1 hour. The resulting reaction mixture was distilled to remove the solvent, and to the residue was added ethyl acetate so that urea was precipitated. The mixture was filtered to remove the urea precipitate, and the remaining organic solution phase was washed with 10% aqueous citric acid, with saturated aqueous sodium bicarbonate and with water, followed by drying said organic solution phase over anhydrous magnesium sulfate. The dried organic solution was distilled under reduced pressure to give a crude (2S,3R)-3-[N-(t-butoxycarbonyl-5-acetoamidomethyl-L-cysteinyl)]amino-2-hydroxy-4-phenylbutanoic acid methyl ester (215 mg).

(B) The compound (215 mg) thus obtained in the step (A) above was dissolved in methanol (2 ml), and the solution was admixed with 1N aqueous potassium hydroxide (0.52 ml) and stirred for 18 hours. After this, 1N aqueous sodium hydroxide was added to the solution, followed by stirring further for 3 hours. The reaction solution was distilled under reduced pressure to remove the methanol. To the residue obtained was added water (10 ml), and the resultant aqueous mixture was washed twice with ethyl ether. The aqueous phase was adjusted to pH 3 by addition of powdery citric acid under ice-coolig and was extracted with ethyl acetate.

The extract in ethyl acetate was washed with saturated aqueous sodium chloride, dried over anhydrous magnesium sulfate and then distilled to remove the solvent. The solid residue obtained was pulverized by addition of ethyl ether, and a white crystalline powder (228 mg) was obtained. To this crystalline powder were added anisol (0.1 ml) and trifluoroacetic acid (0.72 ml) under ice-cooling, followed by stirring for one hour. The reaction mixture was concentrated and pulverized by addition of ethyl ether added. There was obtained (2S,3R)-3-[N-(acetoamidomethyl-L-cysteinyl)]amino-2-hydroxy-4-phenylbutanoic acid trifluoroacetate (167 mg) as a powder.

(C) A mixture of the powdery product (134 mg) obtained in the Step (B) above, O-nitrobenzenesulphinyl chloride (57 mg) and acetic acid was stirred for 2 hours, and was allowed to stand under reduced pressure to remove the acetic acid therefrom. The resulting colorless powder was washed with ethyl ether. The mixture of the resulting colorless powder (180 mg), methanol (3 ml), water (2 ml) and triethylamine (0.04 ml) was admixed with dithioerythritol (133 mg) under a nitrogen stream and was stirred for 1.5 hours. The reaction solution was distilled to remove the methanol, and the resulting residue was pulverized by addition of ethyl acetate, and the powder as formed was recovered by centrifugation. The powdery product recovered was suspended in a mixture of ethyl acetate (3 ml) and water (2 ml), and the resulting suspension was adjusted to pH 2 by addition of 1N HCl under ice-cooling. The aqueous phase was separated from the ethyl acetate phase and washed twice with ethyl acetate. The washed aqueous phase was adjusted to a neutral pH by addition of concentrated aqueous ammonia, to precipitate a colorless crystalline powder. The crystals precipitated were recovered by filtration to give the titled compound (120 mg).

EXAMPLE 6

Synthesis of N-{(2S,3R)-3-[N-(acetylthioacetyl)]amino-2-hydroxy-4-phenylbutanoyl}glycine (2S,3R)-AHPA-Gly. [an abbreviation of N-[(2S,3R)-3-amino-2-hydroxy-4-phenylbutanoyl]glycine] (50.4 mg) was added to 1N aqueous sodium hydroxide (0.4 ml) under ice-cooling. The resultant mixture was admixed with chloroacetyl chloride (22.6 mg), and stirred for 10 minutes under ice-cooling and then at ambient temperature for 2 hours. The reaction solution obtained was mixed with a mixture of thiolacetic acid (16.7 mg), potassium carbonate (20 mg) and water (0.2 ml), and then processed in the same way as in Example 1, to give a colorless powder of the titled compound which gave a value of 369 (M+1) in FD mass spectrometry.

EXAMPLE 7

Synthesis of N-{(2S,3R)-3-[N-(acetylthioacetyl)]amino-2-hydroxy-4-phenylbutanoyl}-L-leucine (2S,3R)-AHPA-L-Leu. [an abbreviation of N-[(2S,3R)-3-amino-2-hydroxy-4-phenylbutanoyl]-L-leucine] (616 mg) was added to 1N aqueous sodium hydroxide (4 ml) under ice-cooling. The resultant mixture was mixed with chloroacetyl chloride (226 mg), and stirred for 10 minutes under ice-cooling and further at ambient temperature for 2 hours. The resulting reaction solution was mixed with a mixture of thiolacetic acid (167 mg), potassium carbonate (192 mg) and water (2 ml), and then processed in the same manner as in Example 1, to give the titled compound (367 mg) as a colorless powder. This product gave a value of 425 (M+1) in mass spectrometry.

EXAMPLE 8

Synthesis of (2S,3R)-3-[N-(2-benzoylthiopropionyl)]amino-2-hydroxy-4-phenylbutanoic acid (2S,3R)-AHPA (58.5 mg) was dissolved in 1N aqueous sodium hydroxide (0.6 ml) under ice-cooling. The solution was then admixed with 2-bromopropionyl chloride (51.4 mg) and stirred for 10 minutes under ice-cooling and then at ambient temperature for 2 hours. The resulting reaction solution was mixed with a mixture of thiobenzoic acid (44.4 mg), potassium carbonate (29 mg) and water (0.3 ml), and the resulting mixture was processed in the same manner as in Example 1, to give the titled compound (54.8 mg) as a colorless powder. This product gave a value of 374 (M+1) in FD mass spectrometry.

EXAMPLE 9

Synthesis of (2S,3R)-3-[N-(3-benzoylthiopropionyl)]amino-2-hydroxy-4-phenylbutanoic acid (2S,3R)-AHPA (58.5 mg) was dissolved in 1N aqueous sodium hydroxide (0.6 ml) under ice-cooling. The resulting solution was admixed with 3-bromopropionyl chloride (51.4 mg) and stirred for 10 minutes under ice-cooling and then at ambient temperature for 2 hours. The resulting reaction solution was mixed with a mixture of thiobenzoic acid (44.4 mg), potassium carbonate (29 mg) and water (0.3 ml), and the resulting mixture was processed in the same manner as in Example 1, to afford the titled compound (48.2 mg) as a colorless powder. This product gave a value of 374 (M+1) in FD mass spectrometry.

What we claim is:
1. A 3-[N-(mercaptoacyl)]amino-4-arylbutanoic acid derivative of the general formula (1):

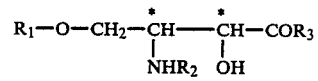

wherein $R_1$ is a hydrogen atom or a hydroxyl group; $R_2$ is an S-substituted or unsubstituted mercaptoloweralkanoyl group of the formula:

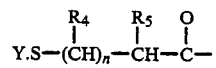

where Y is a hydrogen atom, a lower alkanoyl group or a benzoyl group; n is a whole number of zero or 1; $R_4$ is a hydrogen atom, a lower alkyl group or a phenyl group; $R_5$ is a hydrogen atom, a lower alkyl group, a phenyl group, a hydroxyl group or an amino group; and $R_3$ is a hydroxyl group, a lower alkoxyl group or a glycine residue of the formula —NH'CH$_2$—COOH or a leucine residue of the formula

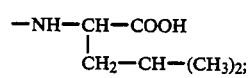

and the asterik (*) denotes the R-configuration or the S-configuration or a combination thereof, or a pharmaceutically acceptable salt of said 3-[N-(mercaptoacyl)-]amino 4-arylbutanoic acid derivative.

2. A 3-[N-(mercaptoalkanoyl)]amino-4-phenyl-butanoic acid of the formula (Ia)

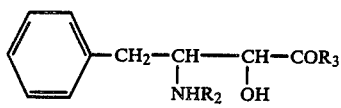 (Ia)

wherein $R_2$ is mercaptoloweralkanoyl group, acetylthioacetyl group, benzoylthioacetyl group, mercaptopropionyl group, acetylthiopropionyl group, benzoylthiopropionyl group, or 2-amino-3-mercaptopropionyl group and $R_3$ is a hydroxyl group, a $(C_1-C_4)$alkoxyl group, a glycine residue of the formula $-NH-CH_2-COOH$ or a leucine residue of the formula

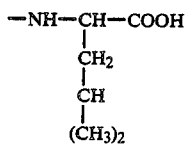

or a pharmaceutically acceptable salt of said 3-[N-(mercaptoalkanoyl)]amino-4-phenylbutanoic acid.

3. A compound of claim 1 which is selected from the following compounds:

(2S,3R)-3-[N-(acetylthioacetyl)]amino-2-hydroxy-4-phenylbutanoic acid; (2S,3R)-3-[N-(mercaptoacetyl)]amino-2-hydroxy-4-phenylbutanoic acid; (2S,3S)-3-[N-(acetylthioacetyl)]amino-2-hydroxy-4-phenylbutanoic acid; (2S,3S)-3[N-(mercaptoacetyl)]amino-2-hydroxy-4-phenylbutanoic acid; (2S,3R)-3-(N-L-cysteinyl)amino-2-hydroxy-4-phenylbutanoic acid; N-{(2S,3R)-3-[N-(acetylthioacetyl)]amino-2-hydroxy-4-phenylbutanoyl}glycine; N-{(2S,3R)-3-[N-(acetylthioacetyl)]amino-2-hydroxy-4-phenylbutanoyl}-L-leucine; (2S,3R)-3-[N-(2-benzoylthiopropionyl)]amino-2-hydroxy-4-phenylbutanoic acid; and (2S,3R)-3-[N-(3-benzoylthiopropionyl)]amino-2-hydroxy-4-phenylbutanoic acid.

4. A pharmaceutical composition for use as an analgesic agent, which comprises as the active ingredient, an analgesically effective amount of 3-[N-(mercaptoacyl)-]amino 4-arylbutanoic acid derivative of the general formula (1):

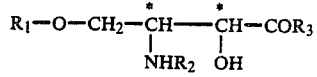

wherein $R_1$ is a hydrogen atom or a hydroxyl group; $R_2$ is an S-substituted or unsubstituted mercaptoloweralkanoyl group of the formula:

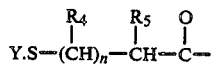

where Y is a hydrogen atom, a lower alkanoyl group or a benzoyl group; n is a whole number of zero or 1; $R_4$ is a hydrogen atom, a lower alkyl group or a phenyl group; $R_5$ is a hydrogen atom, a lower alkyl group, a phenyl group, a hydroxyl group or an amino group; and $R_3$ is a hydroxyl group, a lower alkoxyl group or a glycine residue of the formula $-NH-CH_2-COOH$ or a leucine residue of the formula

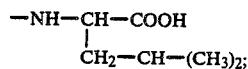

and the asterik (*) denotes the R-configuration or the S-configuration or a combination thereof, or a pharmaceutically acceptable salt of said 3-[N-(mercaptoacyl)-]amino 4-arylbutanoic acid derivative.

5. A method of therapeutically treating an animal feeling pain, including humans feeling pain, which comprises administering to the animal, a compound of the formula (1) as claimed in claim 1 or a compound of the formula (Ia) as claimed in claim 2 or a pharmaceutically acceptable salt thereof, in a non-toxic and effective amount sufficient to reduce or eliminate the pain.

6. A method of enhancing the analgesic activity of a known analgesic compound, [D-ala$^2$,met$^5$]-enkephalin (DAME) when administered to an animal feeling pain, including humans feeling pain, which comprises administering an effective and non-toxic amount of a compound of the formula (1) as claimed in claim 1 or a compound of the formula (Ia) as claimed in claim 2 or a pharmaceutically acceptable salt thereof to the animal, just before or at the same time as when DAME is given to the animal for the analgesic purpose.

* * * * *